United States Patent [19]
Kato

[11] Patent Number: 5,926,926
[45] Date of Patent: Jul. 27, 1999

[54] DISPOSABLE NAPPY, FASTENER FOR THE NAPPY AND RAW MATERIAL FOR THE FASTENER

[75] Inventor: Hisanori Kato, Frankfurt, Germany

[73] Assignee: YKK Corporation, Tokyo, Japan

[21] Appl. No.: 08/806,406

[22] Filed: Feb. 26, 1997

[30] Foreign Application Priority Data

Feb. 27, 1996 [GB] United Kingdom .................. 9604062
May 29, 1996 [GB] United Kingdom .................. 9611140

[51] Int. Cl.⁶ .................................................. A44B 18/00
[52] U.S. Cl. ............................................. 24/442; 604/691
[58] Field of Search ............................ 24/306, 442–452; 604/391, 389; 428/100

[56] References Cited

U.S. PATENT DOCUMENTS

| | | |
|---|---|---|
| 3,955,575 | 5/1976 | Okuda . |
| 4,537,591 | 8/1985 | Coates . |
| 4,568,342 | 2/1986 | Davis . |
| 4,973,326 | 11/1990 | Wood et al. .......................... 24/450 X |
| 5,019,065 | 5/1991 | Scripps .................................. 604/391 X |
| 5,049,145 | 9/1991 | Flug ....................................... 604/391 |
| 5,053,028 | 10/1991 | Zoia et al. ........................... 604/391 X |
| 5,100,399 | 3/1992 | Janson et al. ....................... 604/391 X |
| 5,409,476 | 4/1995 | Coates ................................... 604/391 |
| 5,549,591 | 8/1996 | Landvogt ............................. 604/391 X |
| 5,554,146 | 9/1996 | Niederhofer et al. ............... 24/442 X |

FOREIGN PATENT DOCUMENTS

| | | |
|---|---|---|
| 0 496 567 A2 | 7/1992 | European Pat. Off. . |
| 2 254 998 | 10/1992 | United Kingdom . |
| 2 257 895 | 1/1993 | United Kingdom . |

*Primary Examiner*—James R. Brittain
*Attorney, Agent, or Firm*—Hill & Simpson

[57] ABSTRACT

A disposable diaper has a hook or loop fastener comprising panels of loop material on the front section of the diaper, and panels of hook material on the rear section of the diaper. To hold the panels in a closed position when the diaper is packed, a panel of loop materials is attached to the rear section of the diaper.

25 Claims, 6 Drawing Sheets

DISPOSABLE NAPPY, FASTENER FOR THE NAPPY AND RAW MATERIAL FOR THE FASTENER

BACKGROUND OF THE INVENTION

1. Field of the Invention

The present invention relates to a disposable diaper having a hook and loop fastening system in a fastening portion, a hook and loop fastener to be used for the diaper, and a raw material of the same. This disclosure of the invention uses the term "nappy" and "diaper" interchangeably. Accordingly, the term "nappy" refers to a "diaper".

2. Description of the Related Art

Disposable nappies using fastening tapes which are secured by pressure sensitive adhesive are well known. These disposable nappies suffer from the drawback that contamination of the adhesive with powder, oil, etc. when fitting the nappy impairs the fastening, and of course, it would be impossible to wear it repeatedly. Also, it is difficult to provide a re-usable fastening tape which allows the nappy to be checked and re-fitted.

Disposable nappies using hook and loop fastening systems have been proposed, for example in U.S. Pat. No. 4,894,060. A difficulty with the hook and loop fastening system is the need to keep the cost of the fastener very low, and to allow automated manufacture of the fasteners and to attach the fasteners automatically to the nappy.

SUMMARY OF THE INVENTION

Therefore, an object of the invention is to provide a disposable nappy, fastening function of which would not be impaired so as to realize repetitive fastening and which can be manufactured efficiently at a low cost, a fastener for the nappy and a raw material for the fastener.

The above object is accomplished by a first aspect of the invention which provides a disposable nappy having a hook and loop fastener for securing said nappy to a wearer, and the nappy is characterized by that the fastener is composed of: a first engaging means having a plurality of first engaging elements of hooks and/or loops, and provided oin an outer surface of a front section of the nappy; and a securing member comprising a second engaging means having a plurality of engaging elements which releasably engage with said first engaging means, and a third engaging means which releasably engages with said second engaging means, and that said second engaging means is foldable between a closed position in which the engaging elements of the second engaging means engage with the third engaging means and an open position in which said engaging elements can engage with said first engaging means for securing the nappy to the wearer.

Preferably, the second engaging means comprises a first strip having a base member with a plurality of engaging element at one end on one surface, and the other end of the strip is secured onto the nappy. The first strip is adhered onto the nappy by an adhesive. And the third engaging means is provided on one surface of a base material of a second strip, the other surface of the base material being adhered to the nappy, with its one end being attached onto the first strip.

The above object is also accomplished by a second aspect of the invention which provides a hook and loop fastener for a disposable nappy, which is releasably engage with a first engaging means having a plurality of engaging elements of hooks and/or loops and being provided on a front section of the nappy, and the hook and loop fastener is characterized by comprising; at one end on one surface a first strip including a second engaging means having a plurality of engaging elements which are releasably engageable with the first engaging means; and on the other surface a second strip including a third engaging means having a plurality of engaging elements which are releasably engageable with the second engaging means.

And preferably, an adhesive is provided on one surface of the first strip and the second strip, respectively. And one end of the second strip is attached onto one surface of the first strip on which the adhesive is applied.

Further, the foregoing hook and loop fastener can be manufactured efficiently by cutting a raw material of hook and loop fastener for a disposable nappy, which is releasably engageable with a first engaging means having a plurality of engaging elements of hooks and/or loops provided on a front section of the nappy.

According to a first aspect of the raw material, the raw material is characterized by comprising: a continuous lengthy first strip member of polymeric material including a plurality of second engaging means being spaced apart along a length thereof on one surface and each having a plurality of engaging elements; an adhesive provided on the same surface of the first strip in the regions between the spaced apart plurality of second engaging means; and a plurality of cover having a plurality of third engaging means each attached on the one surface at one end and releasably engages with the second engaging means; and that each cover is placed over and engages with each second engaging means.

Accodring to a second typical aspect of the raw material, the raw material of hook and loop fastener for a disposable nappy is releasably engageable with a first engaging means having a plurality of engaging elements of hooks and/or loops provided on a front section of the nappy. The hook and loop fastener is characterized by comprising: a continuous lengthy first strip member of polymeric material including a second engaging means having a plurality of engaging elements, and being provided continuously along a length on one surface thereof; an adhesive provided on the same surface in the regions adjacent to at least the second engaging means of the first strip member; and a continuous cover having on one surface a third engaging means including a plurality of engaging elements releasably engagable with the second engaging means, and on the other surface an adhesive; and that the cover is placed on the second engaging means so as to engage the third engaging means with the second engaging means.

And preferably, an adhesive is applied entirely on the one surface of the first strip, and the second engaging means is a panel having engaging elements adhered to the strip member. And from an economical point of view, it is preferable that the engaging elements of the second engaging means are consisted of molded hooks. Further, the cover is provided with an adhesive on one surface thereof opposite to the surface having the third engaging means of the cover. And the other surface of the first strip member has a layer to prevent adhesion with the adhesive, and the continuous plurality of engaging assemblies are rolled up.

According to a fourth aspect of the invention, there is provided a disposable nappy having a hook and loop fastener for securing the nappy to a wearer, the fastener being characterized by comprising: a first engaging portion having first engaging elements of hooks and/or loops being provided on an outer surface of a front section of the nappy; and a third engaging portion including a second engaging means having engaging elements which are releasably engageable with the first engaging portion and a part of which is attached onto a rear section of the nappy, and a third engaging means being connected to the second engaging means, having engaging elements engageable with the second engaging means, and attached on to the rear section of the nappy; and that the second engaging means is foldable to take either of a closed position in which the second engaging means is engageable with the third engaging means and an open position in which the second engaging means is engageable with the first engaging portion for securing the nappy to the wearer.

DETAILED DESCRIPTION OF THE PREFERRED EMBODIMENTS

Preferred embodiments of the invention will be described in detail with reference to the accompanying drawings.

Figure 1:
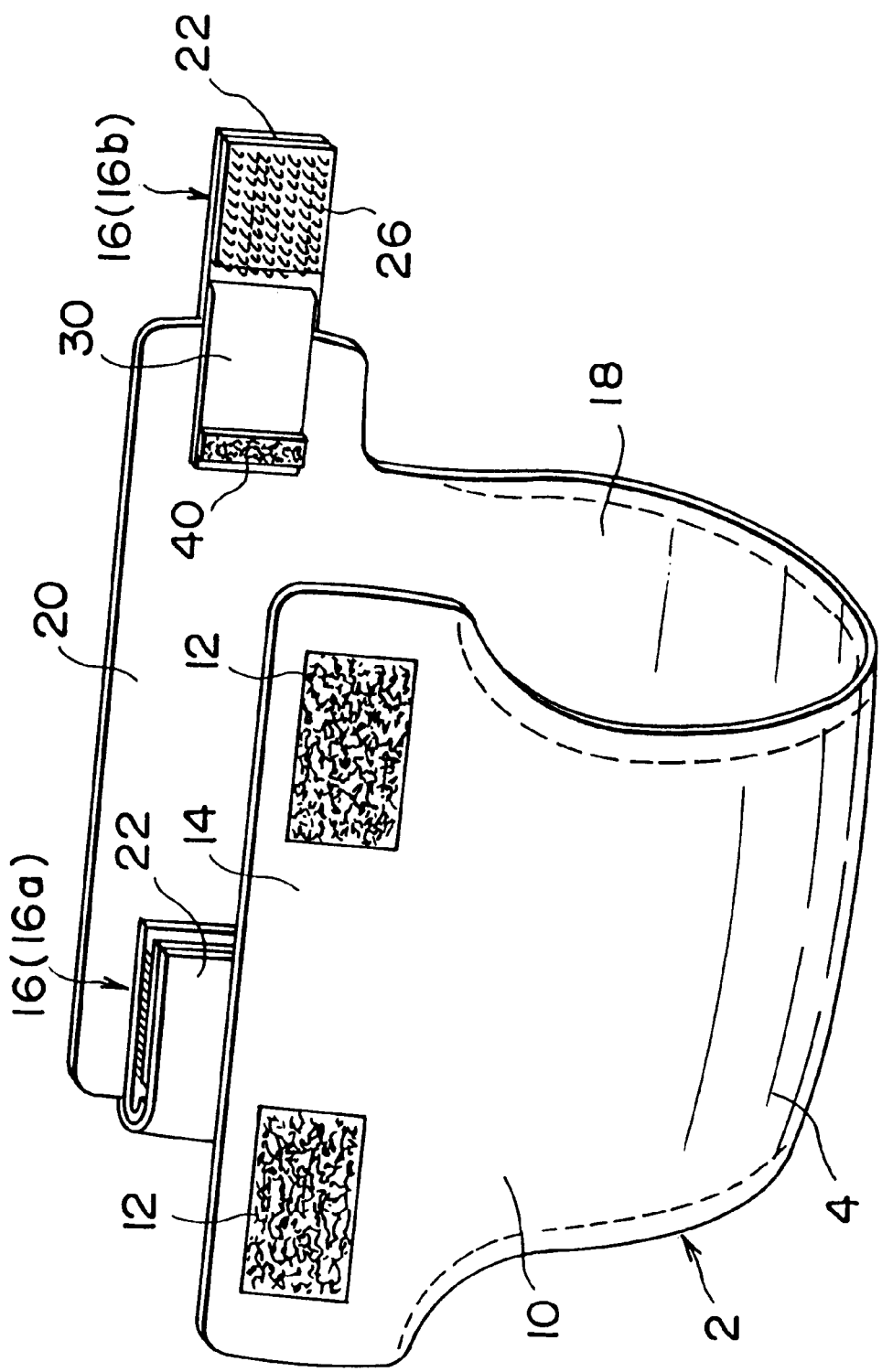
FIG. 1 shows a general structure of a nappy having hook and loop fasteners in accordance with a first embodiment of the invention.

FIG. 1 shows a disposable nappy 2 which comprises a laminated structure having outer layer 4 which hardly allows liquid to permeate, a porous inner layer 6 and a middle layer 8 of absorbent material sandwiched between. The general structure of such nappies is well known in the art and the nappy of this invention described herein is not limited to any particular structure, but rather is characterized by a fastener for securing the nappy to such as a baby, an infant, a patient, or an elderly person.

The drawings, in particular the thickness of the layers, are not drawn to scale, in order to better illustrate the adhesive layers.

A front section 10 of the nappy 2 has two panels 12 of loop material adhered to the outer layer 4 at a waist region 14. Typically the loop material has a woven polypropylene base with loops woven into one surface. Many varieties of loop material for hook and loop fastener systems are known, and it is desired to use a loop material which is inexpensive and also soft to the touch.

Two hook assemblies 16a, 16b are secured to the rear section 18 of the nappy 2 at a waist region 20. One assembly 16a is shown in the closed position, in which the nappy 2 is packed for the user, while the other assembly 16b has been opened ready for use.

Figure 2:
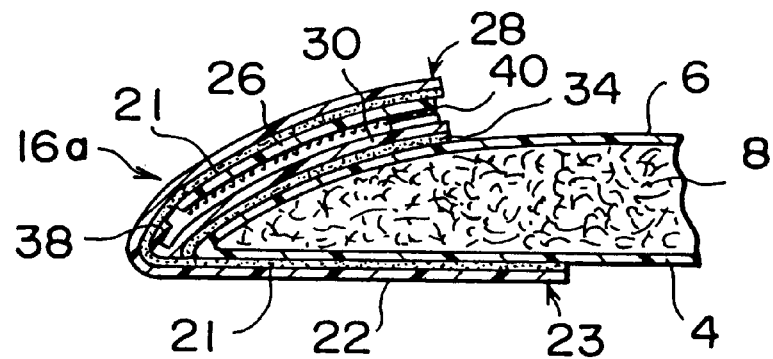
FIG. 2 is a fragmentary cross-sectional view of a hook assembly in a closed position when the nappy is not in use.
Figure 3:
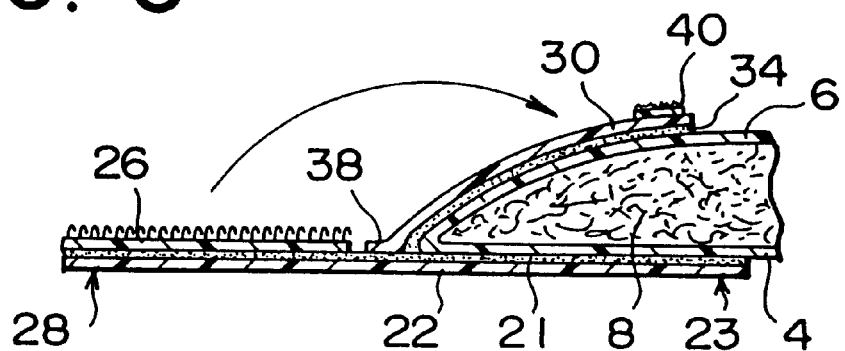
FIG. 3 is a fragmentary cross-sectional view of the hook assembly in an open position when the nappy is in use.

Referring to FIGS. 2 and 3, a hook assembly 16 has a base tape 22 formed of flexible polymeric strip having a pressure sensitive adhesive layer 21 on one surface for adhering the base tape 22 at one end 23 to the outer layer 4 of the nappy 2. A panel 26 of hook material is adhered to the other end 28 of the base tape 22 by the adhesive layer 21. A cover 30 of the same material as the base tape 22 has a pressure sensitive adhesive layer 34 on one surface thereof and is attached at one end 38 to the base tape 22 between the body of the nappy 2 and the hook panel 26 and is adhered to the inner layer 6 of the nappy 2 by the adhesive layer 34. A small panel 40 having loops is attached, by adhesive, to the cover 30 and hooks on the panel 26 engage the loop panel 40 to hold the assembly 16 in the closed position (FIG. 2). To use the fastener, the hook panel 26 is peeled away from the small loop panel 40, to expose the hooks and make them ready for engagement with the loop panels 12 (FIG. 3).

The hook panel 26 is preferably formed of small molded hooks having a rounded profile, to feel comfortable to the touch. Needless to say, mushroom shaped hooks and cut filament type hooks could also be used.

The manufacture of the hook assemblies 16a, 16b, will now be described with reference to FIGS. 4 to 8.

Figure 4:
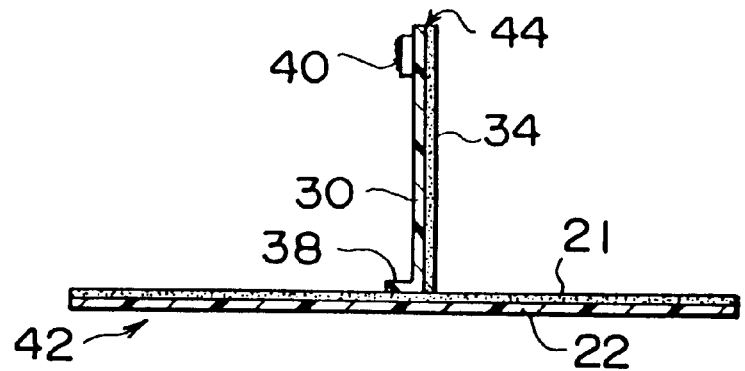
FIG. 4 is a view showing a process for attaching a cover in manufacturign of the hook assembly of the fastener according to the first embodiment of the invention.

In FIG. 4 the continuous base tape 22 has the pressure sensitive adhesive layer 21 on one surface. The other surface 42 is treated so that it will not normally stick to the adhesive layer 21. For example a silicone coating may be applied to the surface 42. Such adhesive tapes are well known in the art.

The cover 30 is formed from the same polymeric material as base tape 22 and has the pressure sensitive adhesive layer 34 on one surface and is attached at the one end 38 to the base tape 22 by pressing the one end 38 onto the adhesive layer 21. The small panel 40 having loops is adhered to an outer end 44 of the cover 30. The smapp panel 40 can be manufactured with a coating of pressure sensitive adhesive on its underside, to adhere to the cover 30.

It will be appreciated that the cover 30 may be formed by applying the plurality of small panels 40 having loops at predetermined positions along a length of the cover 30 and then cutting the cover 30 to form the discrete covers 30.

Figure 5:
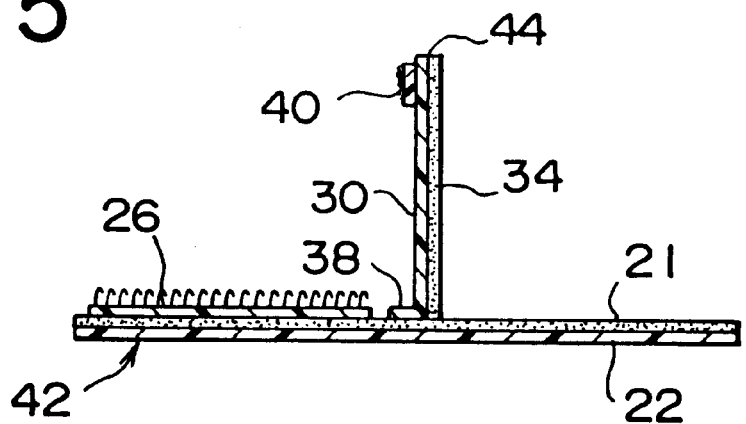
FIG. 5 is a view showing a process for attaching a hook panel of the assembly.
Figure 6:
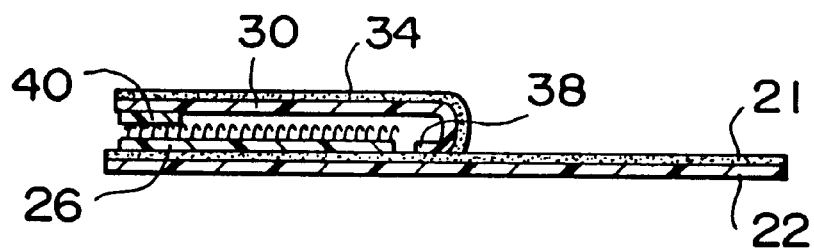
FIG. 6 is a view showing the hook panel and the cover in engagement.
Figure 7:
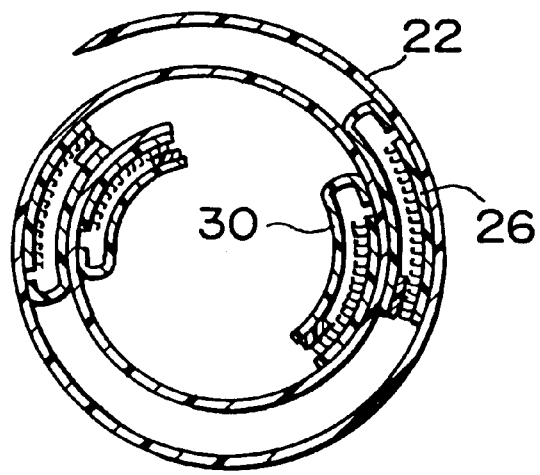
FIG. 7 is a cross-sectional view showing a rolled up long product of the hook assembly manufactured continuously.
Figure 8:
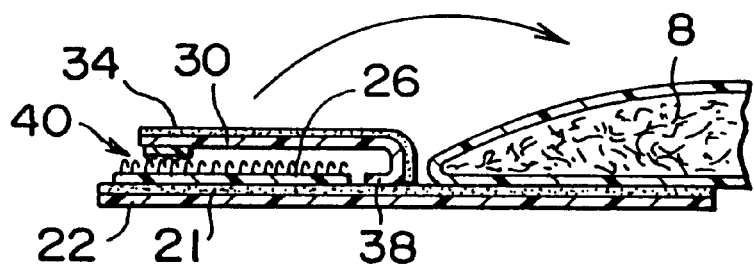
FIG. 8 is a fragmentary cross-sectional view showing a step for attaching the hook assembly onto the nappy.

Referring to FIG. 5, the hook panel 26 is secured to the base tape 22 by pressing onto the adhesive layer 21 formed on the base tape 22, adjacent the cover 30. The cover 30 is then folded over to engage the loop panel 40 with the hook panel 26 (FIG. 6). The continuous base tape 22 can thus be formed with numerous assemblies 16 along its length and rolled for storage or shipment to the nappy manufacturer, as shown in FIG. 7. The silicone treated surface 42 of the base tape 22 contacts the adhesive layer 34 on the cover 30, and simultaneously faces the adhesive layer 21 of the base tape 22. And since the surface 42 is silicone treated, the base tape 22 does not adhere to either of them, and so the tape can be unrolled without damaging the assemblies 16. At the nappy manufacturing stage, the base tape 22 is cut into discrete fastener lengths and secured to the outer layer 4 of the nappy 2 by adhesion (FIG. 8). The hook assembly 16 is then folded over, to press the adhesive layer 34 of the cover 30 against the inner layer 6 of the nappy 2 as shown in FIG. 2. As explained above, the user peels the hook panel 26 away from the small panel 40 having loops to make the hook panel 26 ready for use to secure onto the nappy.

Various modifications may be made to the described embodiment. For example, the hook panel 26 may be integrally formed with the adhesive layer 21 by forming areas of hooks at staggered intervals along the length of the continuous base tape 22, and applying adhesive to the regions between the areas of hooks at similarly staggered intervals. In manufacturing such base tape 22, a method of simultaneously molding hooks on a base material is effective, but the base material may be manufactured by knitting or weaving. In this case, the cover 30 need not be attached at its end 38 to the base tape 22.

The small panel 40 having loops may be provided inward of the end of the cover 30, leaving a flap at the outer end of the hook panel 26, to facilitate peeling of the panel 26 away from the small panel 40.

Also, the loop panels 12 to be attached onto the front section 10 may be substituted by panels having hooks, in which case the panels 26 are the ones having loops, and the small panels 40 have a plurality of hooks.

Figure 9:
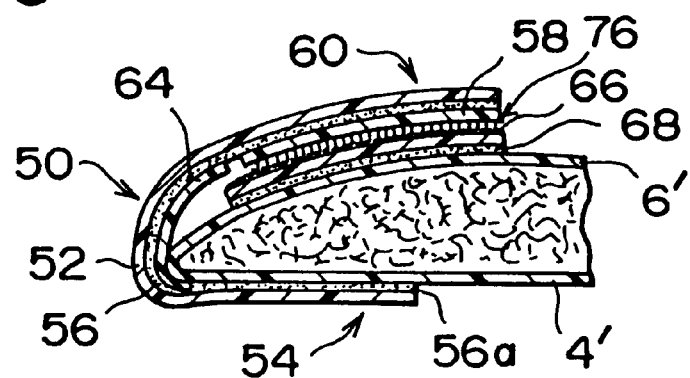
FIG. 9 is a fragmentary cross-sectional view of a second embodiment of the invention.

FIG. 9 shows a second embodiment of a hook assembly of a hook and loop fastener, in the closed position at the time the nappy is not worn. The hook assembly 50 of FIG. 9 comprises a base tape 52 consisted of flexible polymeric material, which is secured at one end 54 by a portion 56a of a layer of pressure sensitive adhesive 56 to an outer layer 4' of a nappy. A hook panel 58 of a hook and loop fastener is secured to the other end 60 of the base tape 52 by the layer of adhesive 56, and a spacing layer 64 of paper is positioned over the central portion of the adhesive 56 on the base tape 52. A loop panel 66 is secured to an inner layer 6' of the nappy by a pressure sensitive adhesive layer 68 and holds the hook panel 58, when the hook assembly 50 is in the closed position (c.f. the hook assembly 16a of FIGS. 1 and 2).

Figure 10:
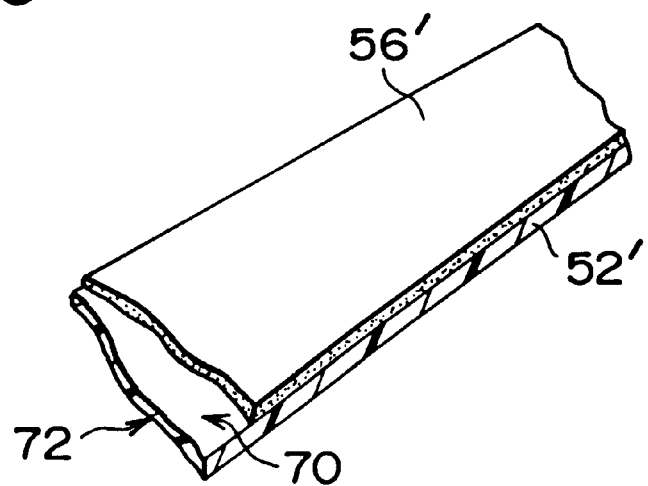
FIG. 10 is a fragmentary cross-sectional view showing the first step for manufacturing a hook assembly according to the invention.

The manfacture of the hook portions 50 will be described with reference to FIGS. 10 to 12. In FIG. 10 a continuous sheet 52' of base tape material has a coating of pressure sensitive adhesive 56' on one major surface 70, and the other surface 72 which will not adhere to the pressure sensitive adhesive 56' is coated with a silicone layer normally.

Figure 11:
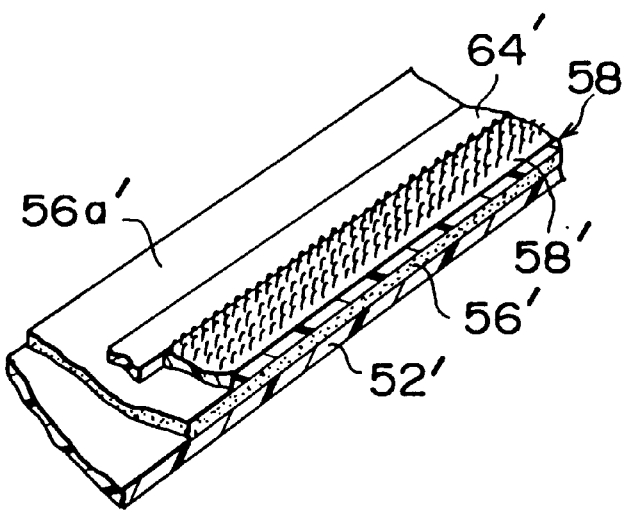
FIG. 11 is a view showing the second step for manufacturing the hook assembly.

In FIG. 11, a hook strip 58' consisting hook panel and a paper strip 64' are adhered to the continuous sheet 52' in alignment along a length thereof by the pressure sensitive adhesive layer 56' with a part of an adhesive layer 56a' being exposed.

Figure 12:
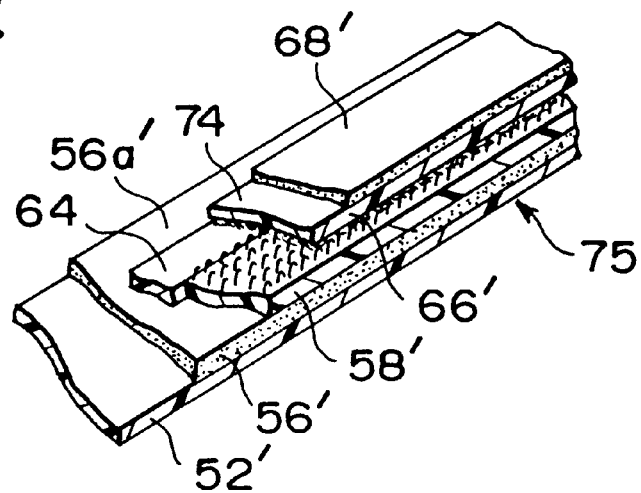
FIG. 12 is a view showing a firnal step for manufacturing the hook assembly.

After completion of adhesion, as shown in FIG. 12, a strip 66' of loop material having a layer 68' of pressure sensitive adhesive on its back surface 74 is then secured over the strip 58' of hook panel material while the pressure sensitive adhesive layer 68' being exposed.

A completed continuous strip 75 of FIG. 12 can be rolled up in the length direction with respective adhesive layers 68', 56a' being inside, though the silicone treated surface 72 of the continuous sheet 52' contact the adhesive layer 68' on the loop strip 66' and the exposed adhesive layer 56a' on the continuous sheet 52'. This is because a rear surface of the continuous sheet 52' is coated with silicone so as not to adhere.

Instead of silicone treatment, a cover sheet (not shown) treated with release agent, may be laid over the adhesive layer 68' and the exposed adhesive layer 56a' before the continuous strip 75 is rolled.

The manufactured roll can be shipped to the nappy manufacturer in this form and is unrolled and cut across its width for forming the hook assemblies 50. The exposed adhesive layer 56a' is pressed against the outer layer 4' of the nappy 2 to secure the hook assembly 50 in place and further the hook assembly 50 is folded around the edge of the nappy 2 to be attached as being engaged with the loop panel 66 adhered to the inner layer 6' as shown in FIG. 9.

Again, it will be appreciated that the loop panel 66 of the foregoing embodiment may stop short of an outer end 76 of the panel 58 to facilitate peeling of the panel 58 from the loop panel 66. Also, the hook panels 58 may be substituted by loop panels, and the loop panels 66 may be substituted by hook panels, or mixed hooks and loops may be provided on the panels.

Figure 13:
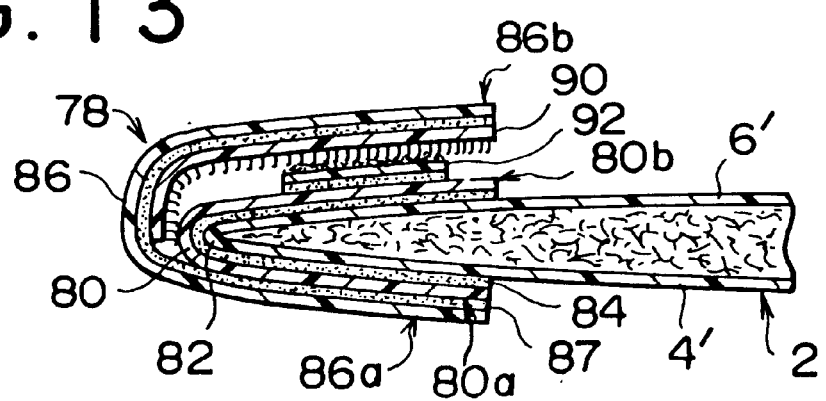
FIG. 13 is a fragmentary cross-sectional view of a nappy according to a third embodiment of the invention.

An embodiment shown in FIG. 13 is similar to the embodiment of FIG. 9, but the paper strip 64' is omitted, and the addition of a relative stiff backing strip 80 which adheres to the nappy 2.

The backing strip 80 extends around an edge 82 of the nappy 2 at the join between the layers 4', 6' of the nappy 2 inwardly and outwardly and is adhered to the outer and inner layers 4', 6' of the nappy 2 by a pressure sensitive adhesive layer 84. A base tape 86 is adhered at one end 86a to an end 80a of the backing strip 80 by a pressure sensitive adhesive 87 and carries a hook panel 90 which extends from the other, outer end 86b of the base tape 86 up to the edge 82 of the nappy 2. A small panel 92 having loops is attached to the backing strip 80 a little short of the other end 80b of the backing strip 80 and of the outer end of the hook panel 90 and releasably engages with the book panel 90.

Figure 14:
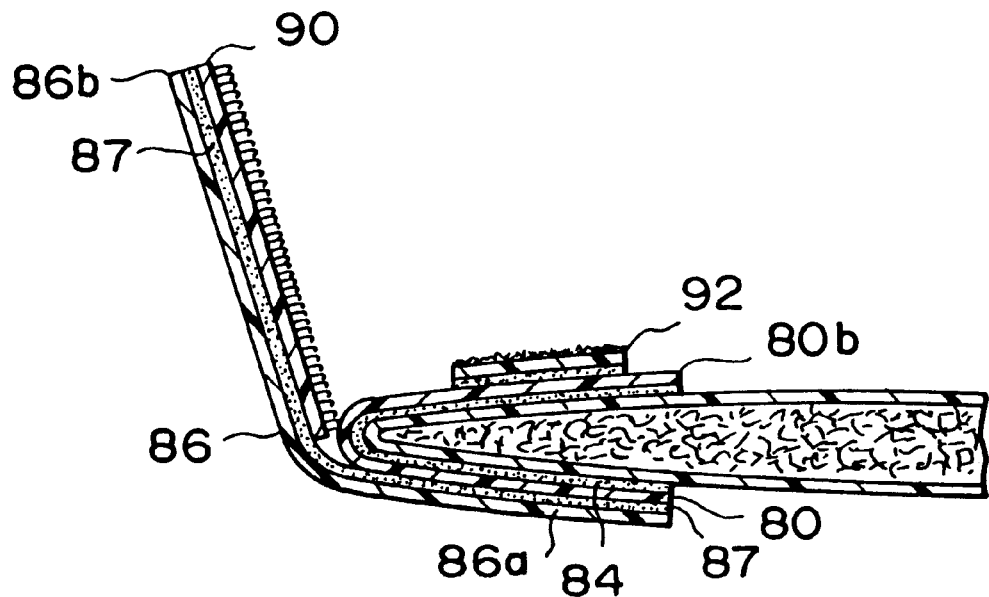
FIG. 14 is a fragmentary cross-sectional view of a hook assembly in a closed position when the nappy is not in use, of the third embodiment.

FIG. 14 shows the hook assembly 78 of FIG. 13 opened out.

Figure 15:
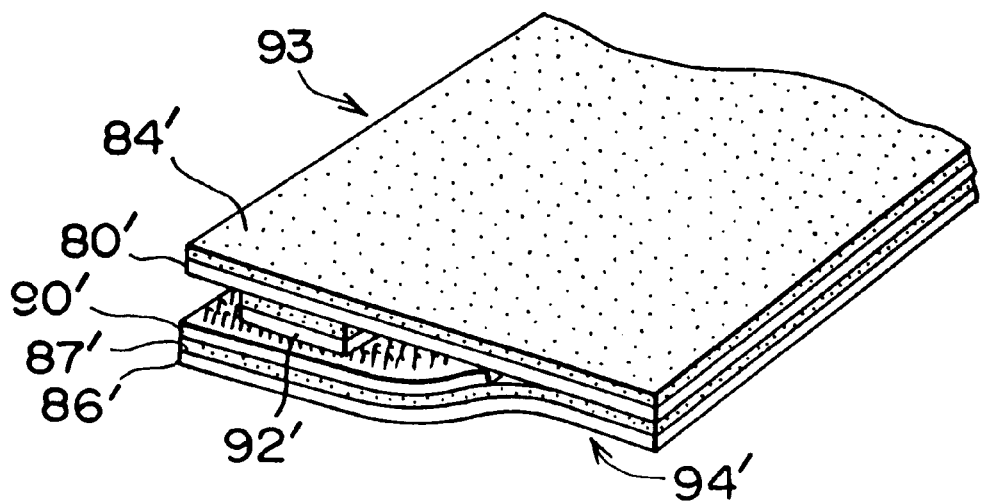
FIG. 15 is a perspective view of an end of a continuous strip of the hook assembly, showing a general structure of the strip.

FIG. 15 shows a continuously manufactured continuous strip 93 which is cut across its width to form the hook assembly 78. A base tape portion 86' has its exposed surface 94', opposite to the surface with hooks, being silcone treated so that the continuous strip 93 can be rolled up for shipment. The continuous strip 93 is then cut across its width to form the hook assemblies 78.

What is claimed is:

1. A disposable diaper having a hook and loop fastener for securing said diaper to a wearer, said diaper being composed of:

a first engaging means having a plurality of first engaging elements of hooks and/or loops, and provided on an outer surface of a front section of the diaper; and a securing member comprising a second engaging means attached to an outer surface of a back section of the diaper from an edge of the diaper to a location substantially inward from the edge and having a plurality of engaging elements which releasably engage with said first engaging means, and a third engaging means attached to an inner surface of said back section of the diaper and to the second engaging means, said third engaging means having a plurality of engaging elements separated from said engaging elements of said second engaging means by an area of said third engaging means devoid of engaging elements and which releasably engages with said second engaging means, wherein said second engaging means is foldable between a closed position in which the engaging elements of the second engaging means engage with the third engaging means and an open position in which said engaging elements of the second engaging means can engage with said first engaging means for securing the diaper to the wearer.

2. A disposable diaper according to claim 1, wherein said second engaging means comprises a first strip having a base member with a plurality of engaging elements at one end on one surface, and the other end of said strip is secured onto the diaper.

3. A disposable diaper according to claim 2, wherein said first strip is adhered onto the diaper by an adhesive.

4. A disposable diaper according to claim 2 or 3, wherein said third engaging means is provided on one surface of a base material of a second strip, the other surface of said base material being adhered to the diaper.

5. A disposable diaper according to claim 4, wherein the base material of said second strip is attached onto the first strip at one end thereof.

6. A hook and loop fastener and a disposable diaper, the hooked loop fastener releasably engageable with a first engaging means having a plurality of engaging elements of hooks and/or loops and being provided on a front section of the diaper, said hook and loop fastener and diaper comprising;
a first strip attached to a back section of the diaper from an edge of the diaper to a location substantially inward from the edge and including a second engaging means having a plurality of engaging elements which are releasably engageable with said first engaging means; and a second strip separate from said first strip, attached to an inside section of the diaper and connected to said first strip and including a third engaging means having a plurality of engaging elements which are releasably engageable with said plurality of engaging elements of said second engaging means.

7. A hook and loop fastener according to claim 6, wherein an adhesive is provided on one surface of said first strip.

8. A hook and loop fastener according to claim 6 or 7, wherein an adhesive is provided on one surface of the second strip.

9. A hook and loop fastener according to claim 6 or 7, wherein one end of said second strip is attached onto one surface of said first strip.

10. A raw material of hook and loop fastener for a disposable diaper, being releasably engageable with a first engaging means having a plurality of engaging elements of hooks and/or loops provided on a front section of the diaper, said raw material comprising:
a continuous lengthy first strip member of polymeric material including a plurality of second engaging means being spaced apart along a length thereof on one surface and each having a plurality of engaging elements;
an adhesive provided on the same surface of the first strip member in the regions between the spaced apart plurality of second engaging means; and
a plurality of covers having a plurality of third engaging means each attached on said one surface at one end and releasably engages with said second engaging means; and
wherein each cover is placed over and engages with each second engaging means.

11. A raw material according to claim 10, wherein an adhesive is applied entirely on said one surface of said first strip member, and said second engaging means is a panel adhered to said strip member.

12. A raw material according to claim 11, wherein each cover is provided with an adhesive on one surface thereof opposite to the surface having said third engaging means of said cover.

13. A raw material according to claim 11, wherein the other surface of said first strip member has a layer to prevent adhesion with said adhesive, and said continuous plurality of engaging assemblies are rolled up.

14. A raw material according to claim 13, wherein the other surface of said first strip member has a layer to prevent adhesion with said adhesive, and said continuous plurality of engaging assemblies are rolled up.

15. A raw material according to claim 10 or 11, wherein the engaging elements of said second engaging means are consisted of molded hooks.

16. A raw material according to claim 15, wherein the other surface of said first strip member has a layer to prevent adhesion with said adhesive, and said continuous plurality of engaging assemblies are rolled up.

17. A raw material according to claim 15, wherein each cover is provided with an adhesive on one surface thereof opposite to the surface having said third engaging means of said cover.

18. A raw material according to claim 17, wherein the other surface of said first strip member has a layer to prevent adhesion with said adhesive, and said continuous plurality of engaging assemblies are rolled up.

19. A raw material according to claim 10, wherein the other surface of said first strip member has a layer to prevent adhesion with said adhesive, and said continuous plurality of engaging assemblies are rolled up.

20. A raw material according to claim 19, wherein the other surface of said first strip member has a layer to prevent adhesion with said adhesive, and said continuous plurality of engaging assemblies are rolled up.

21. A raw material according to claim 17 or 19, wherein the engaging elements of said second engaging means are consisted of molded hooks.

22. A raw material according to claim 10, wherein each cover is provided with an adhesive on one surface thereof opposite to the surface having said third engaging means of said cover.

23. A raw material according to claim 22, wherein the other surface of said first strip member has a layer to prevent adhesion with said adhesive, and said continuous plurality of engaging assemblies are rolled up.

24. A raw material according to claim 10, wherein an adhesive is applied entirely on said one surface of said first strip member, and said second engaging means is a panel having engaging elements adhered to said strip member.

25. A disposable diaper having a hook and loop fastener for securing the diaper to a wearer, said fastener comprising:
a first engaging portion having first engaging elements of hooks and/or loops being provided on an outer surface of a front section of the diaper; and
a second engaging portion including a second engaging means having engaging elements which are releasably engageable with said first engaging portion and a part of which is attached onto a rear section of the diaper from an edge of the diaper to a location substantially inward from the edge, and a third engaging means being connected to said second engaging means, having engaging elements separated from said engaging elements of said second engaging means by an area of said third engaging means devoid of engaging elements and engageable with said engaging elements of said second engaging means, and attached on to the rear section of the diaper; wherein said second engaging means is foldable to take either of a closed position in which said second engaging means is engageable with said third engaging means and an open position in which said second engaging means is engageable with said first engaging portion for securing the diaper to the wearer.

* * * * *